US012349732B2

(12) United States Patent
Taluskie et al.

(10) Patent No.: US 12,349,732 B2
(45) Date of Patent: Jul. 8, 2025

(54) HEATER FOR AN AEROSOL DELIVERY DEVICE AND METHODS OF FORMATION THEREOF

(71) Applicant: RAI STRATEGIC HOLDINGS, INC, Winston-Salem, NC (US)

(72) Inventors: Karen V. Taluskie, Cary, NC (US); Stephen Benson Sears, Siler City, NC (US); Eric Taylor Hunt, Pfafftown, NC (US); William Robert Collett, Lexington, NC (US); Yi-ping Chang, Greensboro, NC (US); Kristen Dodds Weight, Stow, MA (US); Jeffrey A. Karg, Hopkinton, MA (US); Graham P. Eacock, Westborough, MA (US); Matthew C. Ebbs, Newton-Highlands, MA (US); Robert C. Uschold, Leominster, MA (US); Walker Maclaughlin Sloan, III, Berlin, MA (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 0 days.

(21) Appl. No.: 18/504,740

(22) Filed: Nov. 8, 2023

(65) Prior Publication Data

US 2024/0065330 A1 Feb. 29, 2024

Related U.S. Application Data

(60) Continuation of application No. 17/115,828, filed on Dec. 9, 2020, now abandoned, which is a division of (Continued)

(51) Int. Cl.

*A24F 40/46* (2020.01)
*A24F 40/44* (2020.01)

(Continued)

(52) U.S. Cl.

CPC .............. *A24F 40/46* (2020.01); *A24F 40/44* (2020.01); *A61M 11/041* (2013.01);

(Continued)

(58) Field of Classification Search

None

See application file for complete search history.

(56) References Cited

U.S. PATENT DOCUMENTS 4,945,929 A 8/1990 Egilmex
2013/0213419 A1 8/2013 Tucker et al.

(Continued)

FOREIGN PATENT DOCUMENTS

CN 101878958 11/2010
CN 103300482 9/2013

(Continued)

OTHER PUBLICATIONS

U.S. Appl. No. 14/329,334, filed Jul. 11, 2014, Taluskie et al..
U.S. Appl. No. 16/050,598, filed Jul. 31, 2018, Taluskie et al..
U.S. Appl. No. 17/115,828, filed Dec. 9, 2020, Taluskie et al..

*Primary Examiner* — Katherine A Will

(74) *Attorney, Agent, or Firm* — Womble Bond Dickinson (US) LLP

(57) ABSTRACT

The present disclosure relates to aerosol delivery devices, methods of forming such devices, and elements of such devices. In some embodiments, the present disclosure provides a heating member that can be formed of a heating element conformed to a heater substrate configured as a truncated cone (or similar shape) having a first end of a first size and a second end of greater size. In some embodiments, the disclosure provides methods of forming an aerosol delivery device, which can include providing a shell, providing a heating member formed of a heating element conformed to a substrate, configuring the heating member as a truncated cone (or similar shape) having a first end of a first (Continued)

size and a second end of greater size, and inserting the heating member within the shell.

30 Claims, 5 Drawing Sheets

Related U.S. Application Data application No. 16/050,598, filed on Jul. 31, 2018, now Pat. No. 10,888,115, which is a division of application No. 14/329,334, filed on Jul. 11, 2014, now Pat. No. 10,058,123.

(51) Int. Cl.

| | |
|---|---|
| ***A61M 11/04*** | (2006.01) |
| ***A61M 15/06*** | (2006.01) |
| *A24D 1/22* | (2020.01) |
| *A24F 40/10* | (2020.01) |
| *A61M 16/10* | (2006.01) |

(52) U.S. Cl.

CPC ............... *A61M 15/06* (2013.01); *A24D 1/22* (2020.01); *A24F 40/10* (2020.01); *A61M 16/1045* (2013.01)

(56) References Cited

U.S. PATENT DOCUMENTS

| | | | | |
|---|---|---|---|---|
| 2013/0255702 | A1* | 10/2013 | Griffith, Jr. | A24F 15/01 131/328 |
| 2014/0109905 | A1* | 4/2014 | Yamada | A61M 15/06 128/203.27 |
| 2016/0106155 | A1 | 4/2016 | Reevell | |
| 2016/0128388 | A1 | 5/2016 | Liu | |
| 2017/0006916 | A1* | 1/2017 | Liu | H05B 3/03 |

FOREIGN PATENT DOCUMENTS

| | | |
|---|---|---|
| CN | 203538372 | 4/2014 |
| JP | 2010-003487 | 1/2010 |

* cited by examiner

HEATER FOR AN AEROSOL DELIVERY DEVICE AND METHODS OF FORMATION THEREOF

CROSS-REFERENCE TO RELATED APPLICATIONS

This application is a continuation of U.S. application Ser. No. 17/115,828, filed on Dec. 9, 2020, which is a division of U.S. application Ser. No. 16/050,598, filed on Jul. 31, 2018, now U.S. Pat. No. 10,888,115, issued Jan. 12, 2021, which is a division of U.S. application Ser. No. 14/329,334, filed on Jul. 11, 2014, now U.S. Pat. No. 10,058,123, issued Aug. 28, 2018, each of which is incorporated by reference herein in their entirety.

FIELD OF THE DISCLOSURE

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from tobacco or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. Pub. No. 2013/0255702 to Griffith Jr. et al., and U.S. patent application Ser. No. 13/647,000 to Sears et al., filed Oct. 8, 2012, which are incorporated herein by reference in their entirety. See also, for example, the various types of smoking articles, aerosol delivery devices, and electrically powered heat generating sources referenced by brand name and commercial source in U.S. patent application Ser. No. 14/170,838 to Bless et al., filed Feb. 3, 2014, which is incorporated herein by reference in its entirety.

It would be desirable to provide a reservoir for an aerosol precursor composition for use in an aerosol delivery device, the reservoir being provided so as to improve formation of the aerosol delivery device. It would also be desirable to provide aerosol delivery devices that are prepared utilizing such reservoirs.

SUMMARY OF THE DISCLOSURE

The present disclosure relates to aerosol delivery devices, methods of forming such devices, and elements of such devices. In some embodiments, the present disclosure provides heaters, heating elements, or the like that may be suitable for use in an aerosol delivery device. For example, in some embodiments the present disclosure provides an aerosol delivery device comprising a heating member formed of a heating element conformed to a heater substrate configured as a truncated cone having a first end of a first size and a second end of greater size.

In various embodiments, the present aerosol delivery devices and elements suitable for use therein can be defined by one or more of the following statements. Specifically, an aerosol delivery device as described above may include one, two, or any number of the following characteristics in any combination.

The heater substrate can comprise a film or membrane underlying the heating element.

The heater substrate can further comprise a film or membrane overlying the heating element (and all or part of the film or membrane underlying the heating element).

One or both of the heater substrate and the film or membrane overlying the heating member can comprise a textured surface. The texturing can be configured to provide for capillary flow across the textured surface.

The heating member can comprise an electrically conductive ink.

The aerosol delivery device can comprise a porous transport element configured for passage of an aerosol precursor composition along a length thereof, the porous transport element having a first end in a heating arrangement with the heating member.

The truncated cone can include an interior passage therethrough, and the first end of the porous transport element in the heating arrangement with the heating member can be positioned at least partially within the interior passage of the truncated cone.

The first end of the porous transport element in the heating arrangement with the heating member can be positioned so as to at least partially surround the first end of the truncated cone.

The porous transport element can be a fibrous mat.

The porous transport element can be formed of materials, such as carbon fiber, fiberglass, cotton, silk, and the like.

The porous transport element can be formed of natural materials, synthetic materials, combinations of natural and synthetic materials, blends of one or more material types, and blends of one or more fiber types.

The fibrous mat can comprise a plurality of layers.

The fibrous mat can be pleated, can comprise one or more cutouts having one or more different shapes, and can have shaped edges.

The first end of the fibrous mat can comprise fewer layers than the remainder of the fibrous mat.

The porous transport element can comprise central passage through the length thereof.

The aerosol delivery device can comprise an airflow path entering the lesser sized first end of the truncated cone, passing through an interior passage therethrough, and exiting past the greater sized second end of the truncated cone.

The aerosol delivery device can comprise an airflow path exterior to the heating element passing around the truncated cone from the first end thereof past the greater sized second end thereof.

The heating member can be mounted inside a support frame.

The heater substrate can be configured as a frustum.

The heater substrate can be a multifaceted shape.

The porous transport element can comprise a support member passing centrally longitudinally therethrough.

The support member can have an open first end and an open second end and can include one or more passages therethrough.

The support member can comprise one or more air inlets formed in a wall thereof.

The support member can comprise one or more aerosol outlets formed in a wall thereof.

The support member can comprise a flow diverter therein.

In some embodiments, an aerosol delivery device according to the present disclosure can comprise: a shell having an air inlet and a mouthpiece configured for exit of a formed aerosol; a heating member positioned within the shell and being formed of a heating element conformed to a heater substrate configured as a frustum with an interior passage therethrough and having a first end of a first size and a second end of greater size; a porous transport element configured for passage of an aerosol precursor composition along a length thereof, the porous transport element having a first end in a heating arrangement with the heating member; and an airflow path through the shell from the air inlet to the mouthpiece past the first end of the frustum and then past the second, greater sized end of the frustum.

In further embodiments, the present disclosure can provide an atomizer that can be included in an aerosol delivery device. An atomizer, for example, can comprise a heating member formed of a heating element conformed to a heater substrate configured as a truncated cone having a first end of a first size and a second end of greater size. The heating member can be positioned within a support frame. The atomizer also can comprise a porous transport element configured for passage of an aerosol precursor composition along a length thereof, the porous transport element having a first end in a heating arrangement with the heating member. The porous transport element can comprise a support member passing centrally longitudinally therethrough. The atomizer can be configured for insertion into a shell of an aerosol delivery device to be in electrical connection with a power source directly or through one or more electrical contacts, which contacts may comprise part of a connector for connecting the shell to a second shell including a power source.

In some embodiments, the present disclosure can provide methods for forming an aerosol delivery device. The methods can include combining a heating member with a shell of the delivery device, combining the heating member with a porous transport element and a shell, or forming the heating member and the transport element into an atomizer, which can be combined with a shell.

In certain embodiments, a method of forming an aerosol delivery device can comprise: providing a shell; providing a heating member formed of a heating element conformed to a substrate; configuring the heating member as a truncated cone having a first end of a first size and a second end of greater size; and inserting the heating member within the shell.

In various embodiments, the present method for forming an aerosol delivery device can be defined by one or more of the following statements. Specifically, such method as described above may include one, two, or any number of the following characteristics in any combination.

The method can comprise providing a porous transport element configured for passage of an aerosol precursor composition along a length thereof, the porous transport element having a first end and a second opposing end, and configuring the first end thereof in a heating arrangement with the heating member.

The method can comprise contacting the second end of the porous transport element with the aerosol precursor composition.

The truncated cone can include a central passage therethrough, and configuring the first end of the porous transport element in a heating arrangement with the heating member can comprise inserting the first end of the porous transport element into the central passage at the second, greater sized end of the heating member.

The first end of the porous transport element can comprise a central opening therein, and configuring the first end of the porous transport element in a heating arrangement with the heating member can comprise inserting the first, lesser sized end of the heating member into the central opening in the first end of the porous transport element.

The heating member can be formed on the substrate by printing an electrically conductive ink thereon.

BRIEF DESCRIPTION OF THE FIGURES

Figure 1:
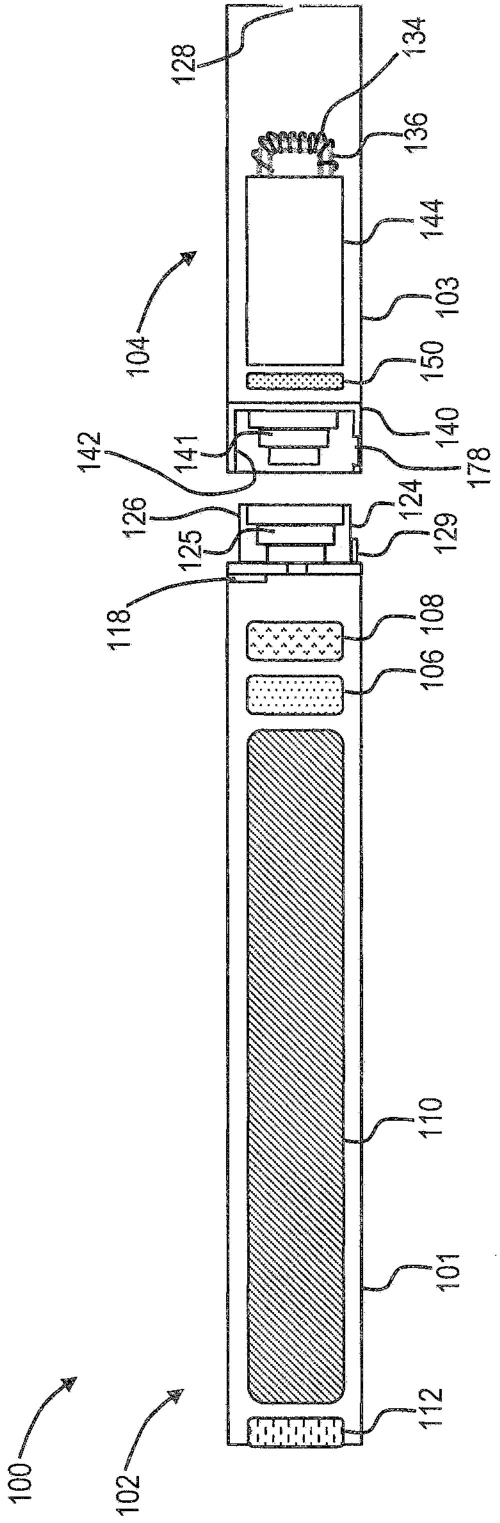
Figure 2:
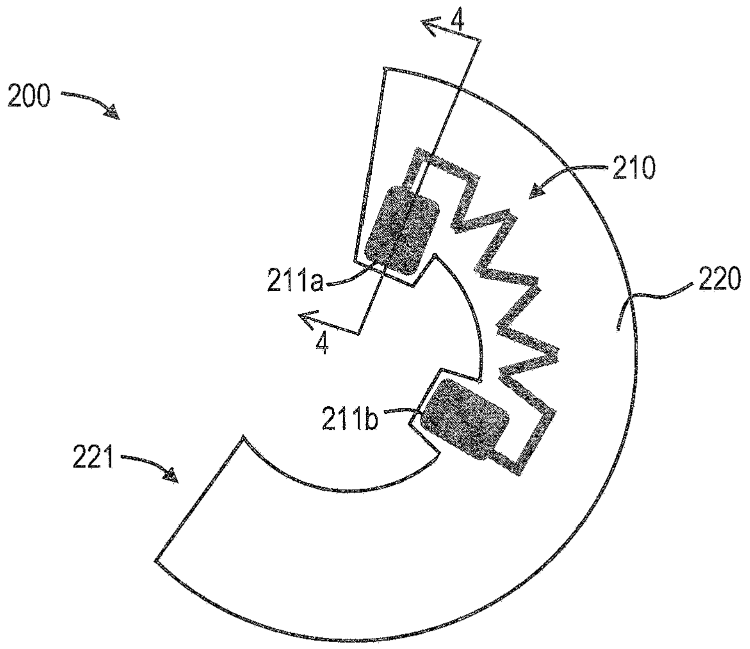
Figure 3:
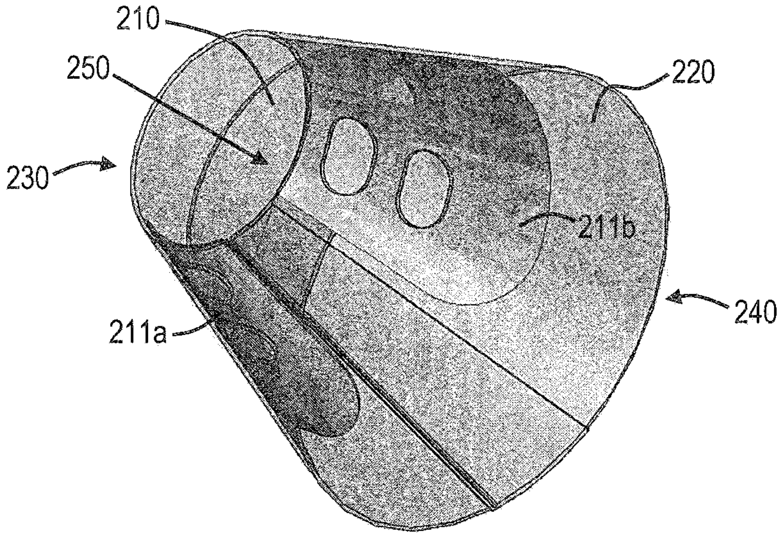
Figure 4:
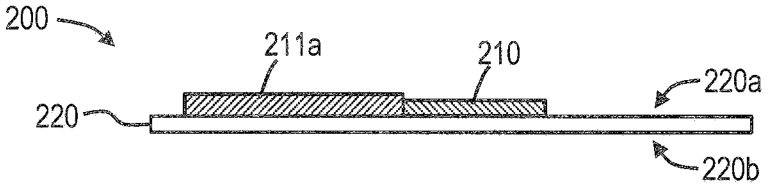
Figure 5:
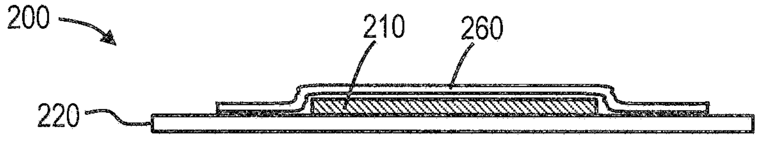
Figure 6:
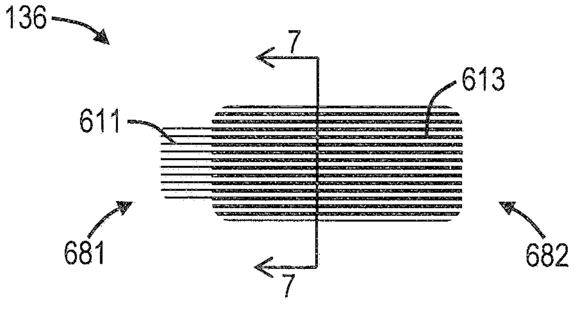
Figure 7:
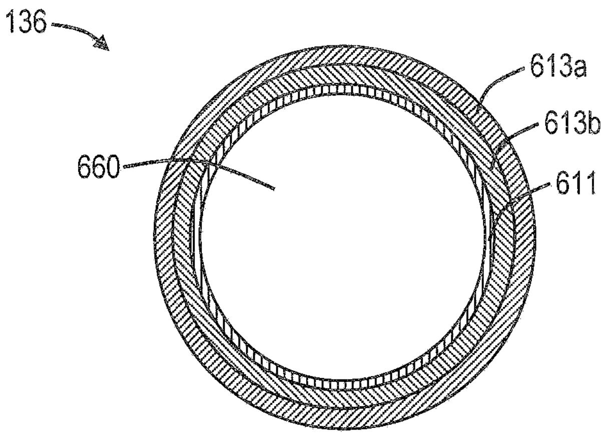
Figure 8:
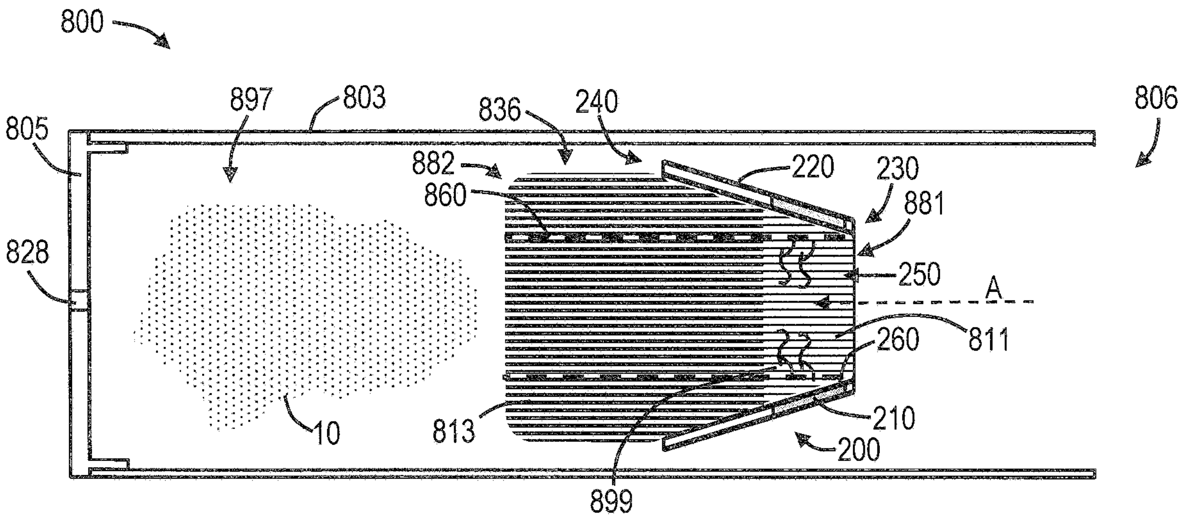
Figure 9:
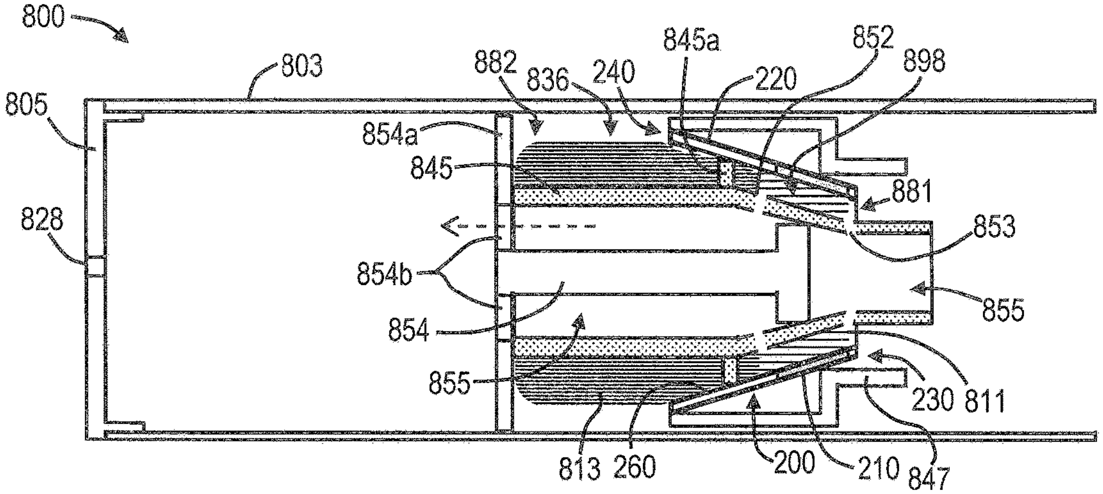
Figure 10:
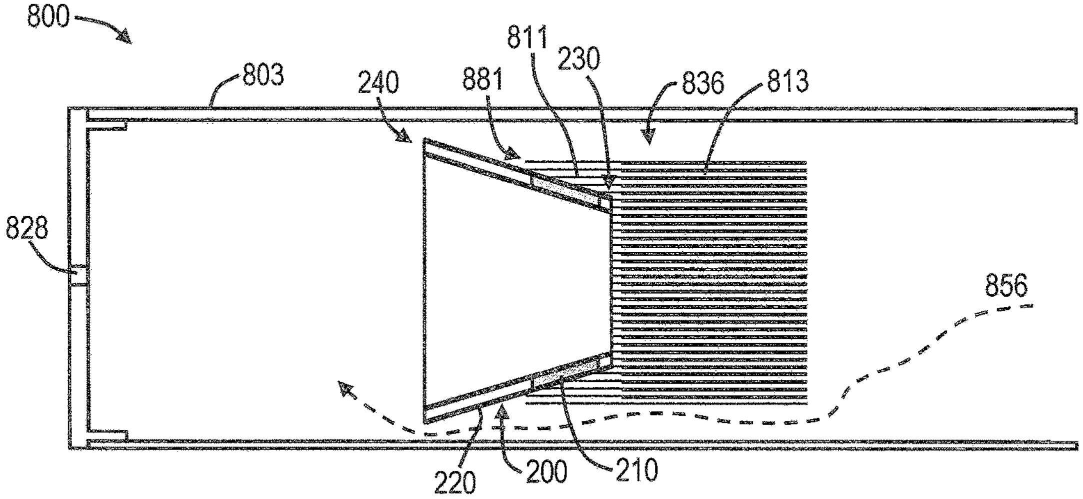

Having thus described the disclosure in the foregoing general terms, reference will now be made to the accompanying drawings, which are not necessarily drawn to scale, and wherein:

FIG. 1 is a partially cut-away view of an aerosol delivery device comprising a cartridge and a control body including a variety of elements that may be utilized in an aerosol delivery device according to various embodiments of the present disclosure;

FIG. 2 is a plan view of a heating member according to an exemplary embodiment of the present disclosure comprising a heating element conformed to a heater substrate;

FIG. 3 is a perspective view of a heating member according to an exemplary embodiment of the present disclosure, the heating member comprising a heater substrate that is curved or folded to form a truncated cone;

FIG. 4 is a cross-section through line 4-4 of the heating member illustrated in FIG. 2;

FIG. 5 is a cross-section of a heating member according to an exemplary embodiment of the present disclosure showing a heating element layered between a heater substrate in the form of a thin film and a heater cover in the form of a thin film;

FIG. 6 is a plan view of a porous transport element according to an exemplary embodiment of the present disclosure, the transport element comprising a first end formed of a single layer of a fibrous mat and a second end formed of a plurality of layers of a fibrous mat;

FIG. 7 is a cross-section through line 7-7 of the porous transport element illustrated in FIG. 6;

FIG. 8 is a partially cut-away view of an aerosol delivery device according to an exemplary embodiment of the present disclosure, the device comprising a heating member configured as a truncated cone and a porous transport element positioned with a first end interior to the heating member, both being configured within a shell;

FIG. 9 is a partially cut-away view of an aerosol delivery device according to an exemplary embodiment of the present disclosure, the device comprising a heating member configured as a truncated cone and a porous transport element positioned with a first end interior to the heating member, the transport element comprising a support member and the heating member comprising a support frame, and all being configured within a shell; and FIG. 10 is a partially cut-away view of an aerosol delivery device according to an exemplary embodiment of the present disclosure, the device comprising porous transport element with a heating member configured as a truncated cone positioned with a first end interior to a first end of the transport element, both being configured within a shell.

DETAILED DESCRIPTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, embodiments of the present disclosure relate to aerosol delivery systems. Aerosol delivery systems according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In preferred embodiments, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing, or the elongated housing can be formed of two or more separable bodies. For example, an aerosol delivery device can comprise an elongated shell or body that can be substantially tubular in shape and, as such, resemble the shape of a conventional cigarette or cigar. In one embodiment, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., a rechargeable battery and various electronics for controlling the operation of that article), and at the other end and removably attached thereto an outer body or shell containing a disposable portion (e.g., a disposable flavor-containing cartridge).

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller or microprocessor), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

In various embodiments, an aerosol delivery device can comprise a reservoir configured to retain the aerosol precursor composition. The reservoir particularly can be formed of a porous material (e.g., a fibrous material) and thus may be referred to as a porous substrate (e.g., a fibrous substrate).

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular embodiments, a cellulose acetate material can be used. In other exemplary embodiments, a carbon material can be used.

One example embodiment of an aerosol delivery device 100 according to the present disclosure is provided in FIG. 1. As seen in the cut-away view illustrated therein, the aerosol delivery device 100 can comprise a control body 102 and a cartridge 104 that can be permanently or detachably aligned in a functioning relationship. Engagement of the control body 102 and the cartridge 104 can be press fit (as illustrated), threaded, interference fit, magnetic, or the like. In particular, connection components, such as further described herein may be used. For example, the control body may include a coupler that is adapted to engage a connector on the cartridge.

In specific embodiments, one or both of the control body 102 and the cartridge 104 may be referred to as being disposable or as being reusable. For example, the control body may have a replaceable battery or a rechargeable battery and thus may be combined with any type of recharging technology, including connection to a typical electrical outlet, connection to a car charger (i.e., cigarette lighter receptacle), and connection to a computer, such as through a universal serial bus (USB) cable. For example, an adaptor including a USB connector at one end and a control body connector at an opposing end is disclosed in U.S. patent application Ser. No. 13/840,264 to Novak et al., filed Mar. 15, 2013, which is incorporated herein by reference in its entirety. Further, in some embodiments the cartridge may comprise a single-use cartridge, as disclosed in U.S. patent application Ser. No. 13/603,612 to Chang et al., filed Sep. 5, 2012, which is incorporated herein by reference in its entirety.

As illustrated in FIG. 1, a control body 102 can be formed of a control body shell 101 that can include a control component 106 (e.g., a microcontroller), a flow sensor 108, a battery 110, and an LED 112, and such components can be variably aligned. Further indicators (e.g., a haptic feedback component, an audio feedback component, or the like) can be included in addition to or as an alternative to the LED. A cartridge 104 can be formed of a cartridge shell 103 enclosing the reservoir 144 that is in fluid communication with a liquid transport element 136 adapted to wick or otherwise transport an aerosol precursor composition stored in the reservoir housing to a heater 134. Various embodiments of materials configured to produce heat when electrical current is applied therethrough may be employed to form the resistive heating element 134. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). Exemplary embodiments of heating members useful in aerosol delivery devices according to the present disclosure are further described below, and such heating members can be incorporated into devices such as illustrated in FIG. 1 as described herein.

An opening 128 may be present in the cartridge shell 103 (e.g., at the mouthend) to allow for egress of formed aerosol from the cartridge 104. Such components are representative of the components that may be present in a cartridge and are not intended to limit the scope of cartridge components that are encompassed by the present disclosure.

The cartridge 104 also may include one or more electronic components 150, which may include an integrated circuit, a memory component, a sensor, or the like. The electronic component 150 may be adapted to communicate with the control component 106 and/or with an external device by wired or wireless means. The electronic component 150 may be positioned anywhere within the cartridge 104 or its base 140.

Although the control component 106 and the flow sensor 108 are illustrated separately, it is understood that the control component and the flow sensor may be combined as an electronic circuit board with the air flow sensor attached directly thereto. Further, the electronic circuit board may be positioned horizontally relative the illustration of FIG. 1 in that the electronic circuit board can be lengthwise parallel to the central axis of the control body. In some embodiments, the air flow sensor may comprise its own circuit board or other base element to which it can be attached. In some embodiments, a flexible circuit board may be utilized. A flexible circuit board may be configured into a variety of shapes, include substantially tubular shapes. In some embodiments, a flexible circuit board may be combined with, layered onto, or form part or all of a heater substrate as further described below.

The control body 102 and the cartridge 104 may include components adapted to facilitate a fluid engagement therebetween. As illustrated in FIG. 1, the control body 102 can include a coupler 124 having a cavity 125 therein. The cartridge 104 can include a base 140 adapted to engage the coupler 124 and can include a projection 141 adapted to fit within the cavity 125. Such engagement can facilitate a stable connection between the control body 102 and the cartridge 104 as well as establish an electrical connection between the battery 110 and control component 106 in the control body and the heater 134 in the cartridge. Further, the control body shell 101 can include an air intake 118, which may be a notch in the shell where it connects to the coupler 124 that allows for passage of ambient air around the coupler and into the shell where it then passes through the cavity 125 of the coupler and into the cartridge through the projection 141.

A coupler and a base useful according to the present disclosure are described in U.S. patent application Ser. No. 13/840,264 to Novak et al., filed Mar. 15, 2013, the disclosure of which is incorporated herein by reference in its entirety. For example, a coupler as seen in FIG. 1 may define an outer periphery 126 configured to mate with an inner periphery 142 of the base 140. In one embodiment the inner periphery of the base may define a radius that is substantially equal to, or slightly greater than, a radius of the outer periphery of the coupler. Further, the coupler 124 may define one or more protrusions 129 at the outer periphery 126 configured to engage one or more recesses 178 defined at the inner periphery of the base. However, various other embodiments of structures, shapes, and components may be employed to couple the base to the coupler. In some embodiments the connection between the base 140 of the cartridge 104 and the coupler 124 of the control body 102 may be substantially permanent, whereas in other embodiments the connection therebetween may be releasable such that, for example, the control body may be reused with one or more additional cartridges that may be disposable and/or refillable.

The aerosol delivery device 100 may be substantially rod-like or substantially tubular shaped or substantially cylindrically shaped in some embodiments. In other embodiments, further shapes and dimensions are encompassed—e.g., a rectangular or triangular cross-section, multifaceted shapes, or the like.

The reservoir 144 illustrated in FIG. 1 can be a container or can be a fibrous reservoir, as presently described. For example, the reservoir 144 can comprise one or more layers of nonwoven fibers substantially formed into the shape of a tube encircling the interior of the cartridge shell 103, in this embodiment. An aerosol precursor composition can be retained in the reservoir 144. Liquid components, for example, can be sorptively retained by the reservoir 144. The reservoir 144 can be in fluid connection with a liquid transport element 136. The liquid transport element 136 can transport the aerosol precursor composition stored in the reservoir 144 via capillary action to the heating element 134 that is in the form of a metal wire coil in this embodiment. As such, the heating element 134 is in a heating arrangement with the liquid transport element 136. Exemplary embodiments of reservoirs and transport elements useful in aerosol delivery devices according to the present disclosure are further described below, and such reservoirs and/or transport elements can be incorporated into devices such as illustrated in FIG. 1 as described herein. In particular, specific combinations of heating members and transport elements as further described below may be incorporated into devices such as illustrated in FIG. 1 as described herein.

In use, when a user draws on the article 100, airflow is detected by the sensor 108, the heating element 134 is activated, and the components for the aerosol precursor composition are vaporized by the heating element 134. Drawing upon the mouthend of the article 100 causes ambient air to enter the air intake 118 and pass through the cavity 125 in the coupler 124 and the central opening in the projection 141 of the base 140. In the cartridge 104, the drawn air combines with the formed vapor to form an aerosol. The aerosol is whisked, aspirated, or otherwise drawn away from the heating element 134 and out the mouth opening 128 in the mouthend of the article 100.

The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., the disclosure of which is incorporated herein by reference in its entirety.

The aerosol delivery device can incorporate a sensor or detector for control of supply of electric power to the heat generation element when aerosol generation is desired (e.g., upon draw during use). As such, for example, there is provided a manner or method for turning off the power supply to the heat generation element when the aerosol delivery device is not be drawn upon during use, and for turning on the power supply to actuate or trigger the generation of heat by the heat generation element during draw. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 by Flick; which are incorporated herein by reference.

The aerosol delivery device most preferably incorporates a control mechanism for controlling the amount of electric power to the heat generation element during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. Pub. Nos. 2009/0230117 to Fernando et al. and 2014/0060554 to Collet et al.; and U.S. patent application Ser. No. 13/837,542, filed Mar. 15, 2013, to Ampolini et al. and Ser. No. 14/209,191, filed Mar. 13, 2014, to Henry et al.; which are incorporated herein by reference.

Representative types of substrates, reservoirs or other components for supporting the aerosol precursor are described in U.S. Pat. No. 8,528,569 to Newton; and U.S. patent application Ser. No. 13/802,950, filed Mar. 15, 2013, to Chapman et al.; Ser. No. 14/011,192, filed Aug. 28, 2013, to Davis et al. and Ser. No. 14/170,838, filed Feb. 3, 2014, to Bless et al.; which are incorporated herein by reference. Additionally, various wicking materials, and the configuration and operation of those wicking materials within certain types of electronic cigarettes, are set forth in U.S. patent application Ser. No. 13/754,324, filed Jan. 30, 2013, to Sears et al.; which is incorporated herein by reference.

In some embodiments, the present disclosure provides a heating member that is useful for heating and vaporizing an aerosol precursor composition. The heating member can be particularly suited for providing consistent, rapid vaporization of the aerosol precursor composition while requiring minimal energy input.

An exemplary embodiment of a heating member 200 is illustrated in FIG. 2. As seen therein, the heating member 200 comprises a heating element 210 and a heater substrate 220. The heater substrate can comprise, for example, a film, membrane, or the like underlying the heating element 210. The heater substrate 220 can be formed of any material suitable for supporting a heating element. In some embodiments, the heater substrate 220 can be an electrically insulating material. The heater substrate 220 likewise can be either heat insulating or heat conducting. The heater substrate 220 preferably is heat stable up to at least the temperature achieved by the heating element. Polymeric materials in particular may be used, for example, polyimides. The heater substrate 220 can comprise a material that can be provided in a sheet, film, or membrane form that is substantially flattened and that is configurable into a variety of shapes. The heater substrate 220 alternatively can be a molded or otherwise prefabricated shape. The heater substrate can be formed, for example, from a ceramic. As illustrated in FIG. 2, the heater substrate 220 is a thin film that is in a shape suitable for being configured into a three-dimensional structure as otherwise described herein. The heater substrate 220 can vary in thickness. For example, heater substrate thickness can be less than 2 mm, less than 1 mm, or less than 0.75 mm. In some embodiments, heater substrate thickness can be about 0.1 mm to about 2 mm, about 0.2 mm to about 1.5 mm, or about 0.25 mm to about 1.25 mm.

The heating element 210 can comprise a metal or like material as otherwise described herein suitable for providing resistive heating. The heating element 210 can be combined with the heater substrate by any suitable means, such as by etching techniques, printing techniques, or adhering techniques. For example, a metal ribbon can be laminated or otherwise affixed to the heater substrate. As a further example, an electrically conductive ink can be printed on the surface of the heater substrate. A heating element comprising an electrically conductive ink can be configured in a variety of patterns of varying complexity, and the ink can be patterned in a manner that can improve aerosol formation. Printing of an electrically conductive ink on the heater substrate can improve manufacturing in that fewer materials and/or fewer processing steps may be required, and high throughput printing techniques can be utilized to rapidly prepare the heating member. Printed heating elements can be textured.

The heating element 210 can include electrical terminals 211*a* and 211*b*. The heating element can be substantially conformed to the heater substrate in that the heating element substantially bends, curves, flexes, or the like to substantially take on the shape of the heater substrate. For example, as further described herein, the heater substrate may be curved upon itself or similarly wrapped to form a hollow frustum or other truncated cone configuration. As the heating element is conformed to the heater substrate, the heating element is adapted to curve as the heater substrate is formed into the curved shape. In some embodiments, the heating element can be characterized as being adhered to and/or in physical contact with the heater substrate along substantially the entire length of the heating element. In this regard, the heating element can be applied to the heater substrate in a variety of configurations to achieve a desired heating profile, power requirement, heat output, or the like.

As illustrated in FIG. 2, the heating element 210 is conformed to the heater substrate 220 along a partial length of the heater substrate. The portion of the heater substrate on which the heating element is conformed can vary. In some embodiments, the heating element can be present on the heater substrate along substantially the entire length thereof. In the illustrated embodiment, the heater substrate 220 includes a structural arm 221 that does not include the heating element. In practice, when the heater substrate is formed into the desired three dimensional shape, the structural arm 221 can overlap (or underlap) all or a section of the portion of the heater substrate to which the heating element is conformed.

In some embodiments, the heater substrate can be configured as an elongated structure having a first end of a first size and a second end of a greater size. Such elongated structure can be, for example, a cone, a truncated cone, a pyramid, a truncated pyramid, or other similar geometrical shape. In some embodiments, the heater substrate can include an interior passage therethrough. The heating member can have a cross-section that is substantially round, substantially square, substantially rectangular, substantially triangular, polygonal (e.g., 3-10 or 4-8 sides) or the like. A heating member in the form of a truncated cone can have a cone angle of up to about 60 degrees, particularly about 5 degrees to about 50 degrees.

As illustrated in the exemplary embodiment of FIG. 3, the heating member 200 formed of a heating element 210 conformed to a heater substrate 220 is configured as a frustum having a first end 230 of a first size and a second end 240 of greater size. Although the illustrated structure is a frustum in that the first end 230 and second end 240 are substantially parallel, it is understood that there is no requirement that the first and second ends be parallel. When included in an aerosol delivery device, the lesser sized end may be directed toward a mouthend of the device or the greater sized end may be directed to a mouthend of the device. The heating member 200 includes an interior passage 250 therethrough from the first end 230 to the second end 240. In embodiments wherein the heater substrate 220 is a film or membrane that is folded, curved, or otherwise configured into the desired shape, it is understood that the interior passage 250 may have a shape that substantially corresponds to the shape of the configured heater substrate. In other embodiments, the heater substrate may have a first shape (e.g., an exterior shape), and the interior passage may have a second, different shape. For example, the heater substrate can be a molded or 3-D printed element, and the interior passage can be provided in a defined shape of defined dimensions that can be designed to optimize air flow through the device, optimize vapor formation, provide turbulent flow, or the like. As such, the substrate can be pre-formed in the desired shape. The heating element in such embodiments can be conformed to an exterior surface of the molded or printed heater substrate and/or a surface defining the interior passage.

In some embodiments, the heater substrate of the heating member can be configured so that the heating element is in a heating arrangement at the exterior of the heating member, for example on an outer surface of the heating member. In other embodiments, the heater substrate of the heating member can be configured so that the heating element is in a heating arrangement at an interior of the heating member, for example within an interior passage of the heater substrate. With reference to FIG. 3, for example, the heater substrate 220 is wrapped (i.e., curved around) in a direction such that the heating element 210 is interior to the heating member 200. In other words, the heating element 210 is positioned to form a heating arrangement with an aerosol precursor composition that may be directed to the interior passage 250 of the heating member 200. It is understood that in other embodiments the heater substrate may be wrapped or curved in the opposing direction so that the heating element is positioned to form a heating arrangement with an aerosol precursor composition that may be directed to the exterior (particularly an outer surface) of the heating member.

In some embodiments, the heater substrate may be heat insulating, and a heating arrangement thus may be formed by directing an aerosol precursor composition to the side of the heater substrate on which the heating element is conformed. In other embodiments, the heater substrate may be heat conducting, and a heating arrangement thus may be formed by directing an aerosol precursor composition to the side of the heater substrate opposite to which the heating element is conformed. The side of the heater substrate film or membrane on which the heating element is conformed can be referenced as the front side of the heater substrate and the opposing side of the heater substrate can be referenced as the back side of the heater substrate. For example, as seen in FIG. 4 (which shows a cross-section through line 4-4 in FIG. 2), the heating element 210 and electrical terminal 211*a* are on the front side 220*a* of the heater substrate 220, and the back side 220*b* of the heater substrate does not include a further element. If desired, a heating element may be present on both the front side and the back side of the heater substrate.

If desired, the heating member can comprise one or more films, membranes, or the like in addition to the heater substrate. For example, in the embodiment shown in FIG. 5, the heating member 200 comprises a heating element 210 conformed to a heater substrate 220 and includes a heater cover 260. The heater cover can be a film or membrane and can be made of the same material or a different material than the heater substrate. The heater cover can be heat conducting or heat insulating. In some embodiments, the heater substrate can be heat insulating, and the heater cover can be heat conducting. In other embodiments, the heater substrate can be heat conducting and the heater cover can be heat insulating. The heating element can be defined as being sandwiched between two films or membranes of the same or different construction. The heater cover can have a substantially identical thickness to the heater substrate. Alternatively, the heater cover can have a thickness that is greater than the heater substrate thickness or lesser than the heater substrate thickness (as illustrated in FIG. 5). The heating element can be conformed to the heater cover or the heater cover can be applied to the heater substrate without the requirement of being adhered or otherwise attached to the heating element. The heater substrate can have a greater rigidity than the heater cover in some embodiments. Moreover, as the heating element is conformed to the heater substrate, the heater cover likewise can be conformed to the heater substrate such that the heater cover can take on the shape into which the heater substrate is configured. The heater cover can be present across the entirety of the surface of the heater substrate upon which the heating element is conformed. In some embodiments, the heater cover can be present only substantially in the area of the heater substrate to which the heating element is conformed. The heater cover can be characterized as overlying the heating element.

The heater substrate and/or the heater cover (if present) can have a textured surface. Texturing can include any variety of shapes, including stipples, dimples, channels, crosshatching, and the like. Texturing can be useful to retain the aerosol precursor liquid on the surface of the heater substrate and/or heater cover and allow for more complete vaporization. Texturing also can be useful to improve flow of the aerosol precursor liquid to the heating element, such as by providing capillary flow paths across the surface of the heater substrate and/or heater cover. Texturing may substantially conform to the shape of the heating element such that aerosol precursor liquid on the surface of the heater substrate and/or heater cover may be directed (such as by capillary action) across the surface to the precise location of the heating element.

An aerosol delivery device according to embodiments of the present disclosure can comprise a porous transport element that is configured for passage of an aerosol precursor composition along a length thereof. The porous transport element can be formed of any material suitable for providing movement of a liquid, such as via capillary action. The porous transport element can be in fluid communication with a separate reservoir that is configured for storage of a liquid aerosol precursor composition. In some embodiments, the porous transport element can be in fluid communication with a reservoir such that the transport element and the reservoir are in physical contact. In other embodiments, the porous transport element can be sufficiently dimensioned so as to absorptively store the liquid aerosol precursor composition and thus function both as a reservoir and a wick.

The porous transport element can be a fibrous material, such as otherwise described herein, for example a carbon fiber material, a fiberglass material, or the like. The porous transport element can be substantially elongated so as to have at least a first end, and the transport element can be configured so that the first end thereof is in a heating arrangement with the heating member.

In some embodiments, the porous transport element can be substantially in the form of a fibrous mat. Such fibrous mat can be formed of a single layer or can be formed of a plurality of layers. In particular, the transport element can be structured so that the first end of the fibrous mat comprises fewer layers than the remainder of the fibrous mat. For example, the transport element can comprise two or more layers of a fibrous material or different fibrous materials annularly aligned. In some embodiments, the transport element can comprise a substantially tubular fibrous mat with a free first end and with a second end that is at least partially surrounded by a reservoir, which can comprise one or more layers of a fibrous material.

In embodiments comprising a plurality of layers, the layers can comprise different materials exhibiting one or more different properties. For example, an inner layer may exhibit greater wicking than the outer layer so as to promote movement of liquid from the outer layer (which may function substantially as a reservoir layer) to the inner layer (which may function substantially as a wick to transport liquid from the reservoir layer to the heating member).

An exemplary embodiment of a transport element 136 is shown in FIG. 6. In the illustrated embodiment, the transport element 136 comprises a first end 681 and a second end 682. At the first end 681, the transport element 136 comprises a single layer fibrous mat 611. At the second end 682, the transport element 136 comprises a multi-layer fibrous mat 613. As illustrated (see FIG. 6 and FIG. 7), the single layer fibrous mat 611 extends into the multi-layer fibrous mat 613 and thus may be considered to form a layer of the multi-layer fibrous mat. The multi-layer fibrous mat 613 may comprise fibers that are different from the fibers forming the single layer fibrous mat 611. Alternatively, the multi-layer fibrous mat 613 can comprise a plurality of layers of the same fibrous material forming the single layer fibrous mat 611. Because the multi-layer fibrous mat 613 contains a greater bulk of material, the multi-layer fibrous mat may function as a reservoir. Alternatively, a separate reservoir may be combined with the transport element 136.

The transport element 136 of FIG. 6 is further illustrated in the cross-section through line 7-7 shown in FIG. 7. As illustrated, the multi-layer fibrous mat 613 comprises two layers 613*a* and 613*b* with the single layer fibrous mat 611 positioned interior thereto. The plurality of layers thus can be concentric layers. As seen in FIG. 7, the transport element further can comprise a central passage 660 therethrough. Particularly, the central passage can extend along the entire length of the transport element from the first end to the second end. In some embodiments, one or both ends of the transport element may be closed.

A heating member and a porous transport element can be combined in a variety of manners in an aerosol delivery device according to the present disclosure. For example, in the embodiment illustrated in FIG. 8, an aerosol delivery device 800 comprises a shell 803 and a mouthpiece 805 with an opening 828 therein for passage of formed aerosol from the device. The shell 803 can define a single unit that can further include control components and power components, such as illustrated in relation to the control body 102 of FIG. 1. The shell 803 alternatively can define a cartridge (such as cartridge 104 in FIG. 1) having a control body attachment end 806 that can be configured for attachment to a control body and that can include attachment elements, such as described in relation to FIG. 1.

The aerosol delivery device 800 in the embodiment of FIG. 8 further comprises a heating member 200 formed of a heating element 210 conformed to a heater substrate 220 configured as a truncated cone having a first end 230 of a first size and a second end 240 of greater size. The heating member 200 further includes a heater cover 260. The heater substrate 220 and the heater cover 260 are each configured as thin films in the illustrated embodiment such that the heating element 210 is substantially sandwiched between the heater substrate and the heater cover. As illustrated, the heater substrate 220 can be heat insulating, and the heater cover 260 can be heat conducting.

In FIG. 8, the heating member 200 includes an interior passage 250 through the truncated cone formed by the heater substrate 220, the heating element 210, and the heater cover 260. The aerosol delivery device 800 also includes a porous transport element 836 that comprises a first end 881 and a second end 882. The porous transport element 836 is formed of a plurality of layers of a fibrous mat such that a single layer fibrous mat 811 forms the first end 881 of the transport element and multi-layer fibrous mat 813 forms the second end 882 of the transport element. The multi-layer fibrous mat 813 can comprise a portion of the single layer fibrous mat 811 surrounded by at least a second layer of the fibrous mat. In the partial section of FIG. 8, the greater fiber density of the multi-layer fibrous mat 813 cause the single layer fibrous mat 811 to blend therewith and become visually obscured. The first end 881 of the porous transport element 836 is positioned within the interior passage 250 of the heating member 200 so as to be in a heating arrangement with the heating element 210. The porous transport element 836 has an aerosol precursor composition stored therein, particularly within the multi-layer fibrous mat 813. As the heating element 210 is heated, the aerosol precursor composition in the single layer mat 811 at the first end 881 of the transport element 836 is vaporized to form a vapor 899 that mixes with air (see dotted line A) to form an aerosol 10 in the cavity 897 within the shell 803. The vapor forms within the central passage 860 (illustrated by the dashed lines) through the transport element. Thus, in some embodiments, the aerosol delivery device can be defined as comprising an airflow path (flow of air A in FIG. 8) entering the lesser sized first end 881 of the truncated cone formed by the heater substrate 220, passing through an interior passage (e.g., central passage 860 in FIG. 8 or central pathway 855 in FIG. 9), and exiting at the greater sized second end 882 of the truncated cone. The nature of the heater substrate can be particularly beneficial in providing for turbulent airflow that can better entrain formed vapor. The heater substrate alone or in combination with one or more further elements of the aerosol delivery device can be configured to cause air passing therethrough to substantially form a vortex or can be configured to substantially cause laminar air flow.

In some embodiments, further elements may be present. For example, the embodiment illustrated in FIG. 9 is substantially identical to the embodiment of FIG. 8 but includes further structural elements. In particular, the aerosol delivery device 800 of FIG. 9 comprises a support member 845 passing centrally longitudinally through the porous transport element 836 substantially from the first end 881 thereof to the second end 882 thereof. The support member 845 can be tapered at one end thereof and can extend beyond the first end 881 of the transport element 836 (as well as beyond the second end 882 of the transport member). The support member 845 can include a central pathway 855 extending longitudinally therethrough or having an otherwise defined pathway therethrough. In some embodiments, the support member 845 can comprise a flow diverter 854 positioned within at least a portion of the central pathway 855. The flow diverter 854 can be positioned so that air entering the central pathway 855 is diverted through one or more air outlets 853 to the vaporization zone 898 between the heating member 200 and the support member 845 where vapor is formed by heating of the aerosol precursor composition in the porous transport element 836 by the heating element 210. Aerosol formed by the vapor mixing with air then can pass back into the central pathway 855 through one or more aerosol outlets 852 positioned downstream from the one or more air inlets 853. The one or more air inlets 853 and the one or more aerosol outlets 852 can be formed in the wall of the support member 845 and can be one or more apertures, a plurality of perforations, or the like. The flow diverter 854 can comprise a flange **854*a* that can be substantially equal to the inner diameter of the shell 803 or can be shorter, and the flange can include one or more flange apertures 854*b* in alignment with the central pathway 855 to permit flow of air and aerosol therethrough (as shown by the dashed arrow). The support member 845 can include a radial extension 845*a* that can be configured to substantially block airflow around the exterior of the support member downstream from the aerosol outlets 852, particularly preventing passage of formed aerosol from the vaporization zone 898 around the exterior of the support member. The aerosol delivery device 800 further can comprise a heater frame 847 that can substantially surround the heating member 200 and provide structural rigidity thereto. The support member 845 and the heater frame 847 can comprise any material suitable for use in an aerosol delivery device, such as thermoplastics, metals, ceramics, and the like. The heater frame 847 can have an open free end. The heater frame 847 can be configured to substantially encapsulate the heating member 200 and can have minimized contact with the heating member. For example, the heater frame 847 can be configured to be in physical contact with one or both of the first end 230 and the second end 240 of the heating member 200. Such contact can be directly at the respective end or can be in the area of the respective end. The contacts between the heater frame 847 and the heating member 200 can define a void space between the heater frame and the heating member. Such configuration can be beneficial to minimize heat loss from the heating member 200 to other components of the aerosol delivery device 800 other than the porous transport element 836**.

Combinations of certain elements described herein can be configured as an atomizer suitable for use with a variety of aerosol delivery devices. For example, a heating member as described herein can be combined with a wick to form an atomizer. The heating member can particularly be combined with a porous transport element as described herein to form an atomizer. In some embodiments, an atomizer can comprise a heating member, a porous transport element, and one or both of a heater frame and a support member. An atomizer also can comprise electrical contacts.

In further embodiments, the heating member and the porous transport element can be combined differently. For example, in the embodiment illustrated in FIG. 10, the first end 881 of the porous transport element 836 can be positioned so as to at least partially surround the first end 230 of the truncated cone formed by the heater substrate 220 and thus be in a heating arrangement with the heating element 210 of the heating member 200. In such embodiments, a support member (845 in FIG. 9) or a heater frame (847 in FIG. 9) or both a support member and a heater frame can be present. When present, the support member may extend fully or partially through the transport element longitudinally and may extend fully or partially through the heating member. In embodiments exemplified by FIG. 10, the aerosol delivery device 800 can comprise an airflow path 856 that is exterior to the heating element and that passes around the truncated cone formed by the heater substrate 220. The airflow path 856 can pass around the heating member 200 from the first end 230 thereof to the greater sized second end 240 thereof. Vapor thus can be formed outside or exterior to the heating member 200 (as opposed to being formed within an interior passage through the heating member). Formed vapor can be entrained in the air through the airflow path and exit the aerosol delivery device through the opening 828 in the mouthpiece 805.

In some embodiments, the present disclosure further provides methods for forming an aerosol delivery device substantially as described herein. The methods can comprise a variety of steps that are not restricted by order of implementation unless otherwise indicated. In some embodiments, a method of forming an aerosol delivery device can comprise configuring a heating member as described herein and positioning the heating member within a shell. Particularly, the heating member can be configured as a truncated cone having a first end of a first size and a second end of greater size, and the so configured heating member can be inserted within the shell.

In particular embodiments, methods according to the present disclosure can comprise providing a porous transport element configured for passage of an aerosol precursor composition along a length thereof, the porous transport element having a first end and a second opposing end, and configuring the first end thereof in a heating arrangement with the heating member. The methods also can comprise contacting the second end of the porous transport element with the aerosol precursor composition. The truncated cone can include a central passage therethrough, and configuring the first end of the porous transport element in a heating arrangement with the heating member can comprise inserting the first end of the porous transport element into the central passage at the second, greater sized end of the heating member. In some embodiments, the first end of the porous transport element can comprise a central opening therein, and configuring the first end of the porous transport element in a heating arrangement with the heating member can comprise inserting the first, lesser sized end of the heating member into the central opening in the first end of the porous transport element.

The aerosol precursor, or vapor precursor composition, useful in an aerosol delivery device as described herein can vary. Most preferably, the aerosol precursor is composed of a combination or mixture of various ingredients or components. The selection of the particular aerosol precursor components, and the relative amounts of those components used, may be altered in order to control the overall chemical composition of the mainstream aerosol produced by the aerosol generating piece. Of particular interest are aerosol precursors that can be characterized as being generally liquid in nature. For example, representative generally liquid aerosol precursors may have the form of liquid solutions, viscous gels, mixtures of miscible components, or liquids incorporating suspended or dispersed components. Typical aerosol precursors are capable of being vaporized upon exposure to heat under those conditions that are experienced during use of the aerosol generating pieces that are characteristic of the current disclosure; and hence are capable of yielding vapors and aerosols that are capable of being inhaled.

For aerosol delivery systems that are characterized as electronic cigarettes, the aerosol precursor most preferably incorporates tobacco or components derived from tobacco. In one regard, the tobacco may be provided as parts or pieces of tobacco, such as finely ground, milled or powdered tobacco lamina. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

The aerosol precursor may incorporate a so-called "aerosol forming materials." Such materials have the ability to yield visible aerosols when vaporized upon exposure to heat under those conditions experienced during normal use of aerosol generating pieces that are characteristic of the current disclosure. Such aerosol forming materials include various polyols or polyhydric alcohols (e.g., glycerin, propylene glycol, and mixtures thereof). Many embodiments of the present disclosure incorporate aerosol precursor components that can be characterized as water, moisture or aqueous liquid. During conditions of normal use of certain aerosol generating pieces, the water incorporated within those pieces can vaporize to yield a component of the generated aerosol. As such, for purposes of the current disclosure, water that is present within the aerosol precursor may be considered to be an aerosol forming material.

It is possible to employ a wide variety of optional flavoring agents or materials that alter the sensory character or nature of the drawn mainstream aerosol generated by the aerosol delivery system of the present disclosure. For example, such optional flavoring agents may be used within the aerosol precursor to alter the flavor, aroma and organoleptic properties of the aerosol. Certain flavoring agents may be provided from sources other than tobacco. Exemplary flavoring agents may be natural or artificial in nature, and may be employed as concentrates or flavor packages.

Exemplary flavoring agents include vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, licorice, and flavorings and flavor packages of the type and character traditionally used for the flavoring of cigarette, cigar and pipe tobaccos. Syrups, such as high fructose corn syrup, also can be employed. Certain flavoring agents may be incorporated within aerosol forming materials prior to formulation of a final aerosol precursor mixture (e.g., certain water soluble flavoring agents can be incorporated within water, menthol can be incorporated within propylene glycol, and certain complex flavor packages can be incorporated within propylene glycol).

Aerosol precursors also may include ingredients that exhibit acidic or basic characteristics (e.g., organic acids, ammonium salts or organic amines). For example, certain organic acids (e.g., levulinic acid, succinic acid, lactic acid, and pyruvic acid) may be included in an aerosol precursor formulation incorporating nicotine, preferably in amounts up to being equimolar (based on total organic acid content) with the nicotine. For example, the aerosol precursor may include about 0.1 to about 0.5 moles of levulinic acid per one mole of nicotine, about 0.1 to about 0.5 moles of succinic acid per one mole of nicotine, about 0.1 to about 0.5 moles of lactic acid per one mole of nicotine, about 0.1 to about 0.5 moles of pyruvic acid per one mole of nicotine, or various permutations and combinations thereof, up to a concentration wherein the total amount of organic acid present is equimolar to the total amount of nicotine present in the aerosol precursor.

As one non-limiting example, a representative aerosol precursor can have the form of a mixture of about 70% to about 90% glycerin, often about 75% to about 85% glycerin; about 5% to about 20% water, often about 10% to about 15% water; about 1% to about 10% propylene glycol, often about 4% to about 8% propylene glycol; about 0.1% to about 6% nicotine, often about 1.5% to about 5% nicotine; and optional flavoring agent in an amount of up to about 6%, often about 0.1% to about 5% flavoring agent; on a weight basis. For example, a representative aerosol precursor may have the form of a formulation incorporating greater than about 76% glycerin, about 14% water, about 7% propylene glycol, about 1% to about 2% nicotine, and less than about 1% optional flavoring agent, on a weight basis. For example, a representative aerosol precursor may have the form of a formulation incorporating greater than about 75% glycerin, about 14% water, about 7% propylene glycol, about 2.5% nicotine, and less than about 1% optional flavoring agent. For example, a representative aerosol precursor may have the form of a formulation incorporating greater than about 75% glycerin, about 5% water, about 8% propylene glycol, about 6% nicotine, and less than about 6% optional flavoring agent, on a weight basis.

As another non-limiting example, a representative aerosol precursor can have the form of a mixture of about 40% to about 70% glycerin, often about 50% to about 65% glycerin; about 5% to about 20% water, often about 10% to about 15% water; about 20% to about 50% propylene glycol, often about 25% to about 45% propylene glycol; about 0.1% to about 6% nicotine, often about 1.5% to about 5% nicotine; about 0.5% to about 3%, often about 1.5% to about 2% menthol; and optional additional flavoring agent in an amount of up to about 6%, often about 0.1% to about 5% flavoring agent; on a weight basis. For example, a representative aerosol precursor may have the form of a formulation incorporating about 50% glycerin, about 11% water, about 28% propylene glycol, about 5% nicotine, about 2% menthol, and about 4% other flavoring agent, on a weight basis.

Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al. and 2014/0060554 to Collett et al., the disclosures of which are incorporated herein by reference. Other aerosol precursors that may be employed include the aerosol precursors that have been incorporated in the VUSE® product by R. J. Reynolds Vapor Company, the BLU® product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. Typically, the amount of aerosol precursor incorporated within the aerosol delivery system, and particularly within the aerosol generating piece, is less than about 2 g, generally less than about 1.5 g, often less than about 1 g and frequently less than about 0.5 g.

Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; and U.S. patent application Ser. No. 14/173,266, filed Feb. 5, 2014, to Sears et al.; which are incorporated herein by reference.

Yet other features, controls or components that can be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. Nos. 2010/0163063 by Fernando et al.; 2013/0192623 to Tucker et al.; 2013/0298905 to Leven et al.; 2013/0180553 to Kim et al. and 2014/0000638 to Sebastian et al.; and U.S. patent application Ser. No. 13/840,264, filed Mar. 15, 2013, to Novak et al. and Ser. No. 13/841,233, filed Mar. 15, 2013, to DePiano et al.; which are incorporated herein by reference.

The foregoing description of use of the article can be applied to the various embodiments described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article illustrated in FIG. 1 or as otherwise described above may be included in an aerosol delivery device according to the present disclosure.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

That which is claimed is:

1. A heating member arranged to receive an aerosol precursor composition from a storage, the heating member comprising:

a heater substrate having a first side and a second, opposing side and including an interior passage at least partially therethrough, the interior passage being at least partially defined by the second, opposing side of the heater substrate, wherein the heater substrate is configured as an elongated structure having a first end of a first size and a second end of a greater size; and a heating element that is printed, etched, or adhered on the first side of the heater substrate;

wherein the heating member is arranged relative to the storage such that the aerosol precursor composition is directed from the second, opposing side of the heater substrate to the heating element.

2. The heating member of claim 1, wherein the elongated structure has a cross-section that is substantially round, substantially square, substantially rectangular, substantially triangular, or substantially polygonal.

3. The heating member of claim 1, further comprising a film or membrane on the heater substrate.

4. The heating member of claim 3, wherein the film or membrane is conformed to the heater substrate.

5. The heating member of claim 3, wherein the film or membrane and the heater substrate each exhibit different heat properties.

6. The heating member of claim 5, wherein the heater substrate is heat insulating, and the film or membrane is heat conducting.

7. The heating member of claim 5, wherein the heater substrate is heat conducting and the film or membrane is heat insulating.

8. The heating member of claim 3, wherein the heater substrate and the film or membrane have different thicknesses.

9. A cartridge of an aerosol delivery device, the cartridge comprising:

a storage for an aerosol precursor composition; and the heating member of claim 1.

10. The cartridge of claim 9, wherein the heating member has a cross-section that is substantially polygonal.

11. The cartridge of claim 9, wherein the heater substrate is a molded structure.

12. The cartridge of claim 9, wherein the heater substrate is ceramic.

13. The cartridge of claim 9, wherein the heater substrate is a 3-D printed structure.

14. The cartridge of claim 9, wherein the heater substrate has a textured surface.

15. The cartridge of claim 14, wherein the textured surface comprises one or more channels.

16. The cartridge of claim 9, wherein the heater substrate comprises one or more capillary flow paths.

17. The cartridge of claim 9, wherein the heating element is curved.

18. The cartridge of claim 9, wherein the heating element comprises metal.

19. The cartridge of claim 9, wherein the heating element is a metal ribbon.

20. The cartridge of claim 19, wherein the metal ribbon is laminated to the heater substrate.

21. The cartridge of claim 9, wherein the heating element is an electrically conductive ink.

22. The cartridge of claim 21, wherein the heating element is patterned on the first side of the heater substrate.

23. The cartridge of claim 21, wherein the heating element is textured.

24. The cartridge of claim 9, the heating element further comprising electrical terminals.

25. The cartridge of claim 9, further comprising an electrical power source in electronic connection with the heating element.

26. The cartridge of claim 25, further comprising at least one control component configured to control electrical current flow from the power source to the heating element.

27. The heating member of claim 1, wherein the interior passage extends through the second end to the first end of the heater substrate, the aerosol precursor composition being conveyed to the heating element through the interior passage.

28. The heating member of claim 1, wherein the interior passage extends between the second end and the first end of the heater substrate, the aerosol precursor composition being conveyed from the interior passage to the heating element.

29. The heating member of claim 1, wherein the first end is non-parallel to the second end.

30. The heating member of claim 1, wherein the first end is parallel with the second end.

* * * * *